US009999384B2

(12) United States Patent
Mondro et al.

(10) Patent No.: US 9,999,384 B2
(45) Date of Patent: Jun. 19, 2018

(54) SLEEVE FOR REMOVABLE LANCET OF LANCING DEVICE

(75) Inventors: Jason Mondro, Sparta, NJ (US); Kande Horne, Whippany, NJ (US); Sophia Varghese, Nutley, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 658 days.

(21) Appl. No.: 14/003,716

(22) PCT Filed: Mar. 9, 2011

(86) PCT No.: PCT/US2011/000438

§ 371 (c)(1),
(2), (4) Date: Dec. 26, 2013

(87) PCT Pub. No.: WO2012/121686

PCT Pub. Date: Sep. 13, 2012

(65) Prior Publication Data

US 2015/0045824 A1 Feb. 12, 2015

(51) Int. Cl.
*A61B 17/14* (2006.01)
*A61B 5/15* (2006.01)
(Continued)

(52) U.S. Cl.
CPC ........ *A61B 5/150633* (2013.01); *A61B 5/157* (2013.01); *A61B 5/1519* (2013.01); *A61B 5/150022* (2013.01); *A61B 5/15113* (2013.01); *A61B 5/15117* (2013.01); *A61B 5/15194* (2013.01); *A61B 5/150259* (2013.01); *A61B 5/150358* (2013.01); *A61B 5/150519* (2013.01);
(Continued)

(58) Field of Classification Search
CPC .............. A61B 5/1411; A61B 5/15142; A61B 5/15186; A61B 5/15146; A61B 5/15188
See application file for complete search history.

(56) References Cited

U.S. PATENT DOCUMENTS 4,139,011 A * 2/1979 Benoit .................. A61H 39/08 606/182
4,452,243 A 6/1984 Leopoldi
(Continued)

FOREIGN PATENT DOCUMENTS

JP 2005-185825 7/2005
JP 2006-231093 9/2006

OTHER PUBLICATIONS

Extended European Search Report issued in EP Application No. 11860654.0 dated May 8, 2014.
(Continued)

*Primary Examiner* — Tuan V Nguyen
(74) *Attorney, Agent, or Firm* — Dickinson Wright, PLLC

(57) ABSTRACT

A lancing device (121) substantially reduces wobble in a lancet (151) used to lance a site. The lancet (151) is removably received by a cartridge (161), which is movably received by the lancing device (121). The lancet (151) is movable between a first position in which a penetrating member (153) connected to the lancet (151) is unexposed and a second position in which the penetrating member is exposed outside of the lancing device (121) for lancing a site. A spring (171) is connected to the cartridge (161) to return the lancet (151) to the first position after the site is lanced.

19 Claims, 12 Drawing Sheets

192
161
167
190
141
143
153
160
123
121
124
131
122
133
125

(51) Int. Cl.
*A61B 5/151* (2006.01)
*A61B 5/157* (2006.01)

(52) U.S. Cl.
CPC ... *A61B 5/150389* (2013.01); *A61B 5/150412* (2013.01); *A61B 5/150442* (2013.01); *A61B 5/150801* (2013.01)

(56) References Cited

U.S. PATENT DOCUMENTS

| | | | | |
|---|---|---|---|---|
| 4,539,988 | A | 9/1985 | Shirley | |
| 4,677,979 | A | 7/1987 | Burns | |
| 4,735,203 | A | 4/1988 | Ryder | |
| 4,817,603 | A | 4/1989 | Turner | |
| RE32,922 | E | 5/1989 | Levin | |
| 5,350,392 | A | 9/1994 | Purcell | |
| 5,356,420 | A * | 10/1994 | Czernecki | A61B 5/15142 606/181 |
| 5,613,978 | A | 3/1997 | Harding | |
| D393,716 | S | 4/1998 | Brenneman | |
| D393,717 | S | 4/1998 | Brenneman | |
| 5,871,494 | A * | 2/1999 | Simons | A61B 5/1411 606/181 |
| 6,168,606 | B1 | 1/2001 | Levin | |
| 6,464,649 | B1 * | 10/2002 | Duchon | A61B 5/150022 600/583 |
| 6,540,763 | B2 * | 4/2003 | Teo | A61B 5/1411 606/182 |
| D499,182 | S | 11/2004 | Moore | |
| 6,890,319 | B1 | 5/2005 | Crocker | |
| 7,192,405 | B2 | 3/2007 | DeNuzzio | |
| 7,282,058 | B2 | 10/2007 | Levin | |
| 7,494,498 | B2 | 2/2009 | Lipoma | |
| 2004/0186500 | A1 | 9/2004 | Kioke et al. | |
| 2006/0047294 | A1 * | 3/2006 | Mori | A61B 5/150022 606/181 |
| 2009/0105741 | A1 | 4/2009 | Lipoma et al. | |
| 2009/0143810 | A1 * | 6/2009 | Kitamura | A61B 5/1411 606/182 |
| 2010/0036407 | A1 | 2/2010 | Fowler et al. | |
| 2010/0241031 | A1 * | 9/2010 | Lai | A61B 5/1411 600/583 |
| 2011/0098735 | A1 * | 4/2011 | Lamps | A61B 5/1411 606/182 |
| 2011/0106127 | A1 * | 5/2011 | Shin | A61B 5/1411 606/182 |

OTHER PUBLICATIONS

Communication dated Feb. 23, 2017 which issued in the corresponding Patent Application No. 2,829,115.

* cited by examiner 188
187
185
184
181
183
182
159
151
158
152
155
192
156
173
157
171
153
175
166
168
160
167
194
169
196
190
161

SLEEVE FOR REMOVABLE LANCET OF LANCING DEVICE

FIELD OF THE INVENTION

The present invention relates generally to a lancing device having a replaceable lancet. More particularly, the present invention relates to a sleeve for a lancet to facilitate movement of the lancet in a lancing device during lancing. Still more particularly, the present invention relates to a lancet sleeve that is movably connected to a lancing device, thereby facilitating movement of the lancet in the lancing device.

BACKGROUND OF THE INVENTION

Self-monitoring of blood glucose levels, or other diagnostic tests, requires a user to extract a discrete volume of capillary blood (typically from the fingertip) and place the extracted blood on a disposable element for analysis. Accordingly, a lancing device is required to lance the user's finger to obtain the blood sample for testing.

Existing lancing devices include a lancet movably disposed in a housing. A firing mechanism strikes a rear end of the lancet, thereby imparting momentum to the lancet. The lancet travels through the housing such that a lancet stylet exits the housing and punctures a user's skin. When a lancet is not directly attached to the firing mechanism, the lancet is subject to increased wobble during travel as a result of being struck by the firing mechanism. Additionally, the impact of the firing mechanism can cause deformation of the lancet, thereby absorbing some of the energy and resulting in less momentum being transferred to the lancet. The wobble and loss of momentum adversely affect travel of the lancet during lancing, thereby resulting in unstable and non-smooth motion of the lancet. Accordingly, there is a need to reduce or eliminate wobble and loss of momentum in a lancet that is not directly attached to a firing mechanism.

Lancets are also difficult to remove from the housing after lancing. Lancets that are directly connected to the firing mechanism must be disconnected therefrom and the new lancet must be connected to the firing mechanism. Many housings must also be partially disassembled and then reassembled when removing and installing lancets. Furthermore, lancets are limited to being installed in a direction along an axis of the firing mechanism. Accordingly, a need exists for simple and safe installation and removal of lancets from lancing devices.

SUMMARY OF THE INVENTION

In accordance with an aspect of the present invention, a lancet moves smoothly and stably during lancing.

In accordance with another aspect of the present invention, a lancing assembly is quickly and easily installed and removed from the lancing device.

In accordance with another aspect of the present invention, a lancing assembly may be installed in and removed from a lancing device in a direction that is not along an axis of movement of the firing mechanism.

A lancing device in accordance with embodiments of the present invention provides a lancing device that substantially reduces wobble associated with a lancet not directly connected to a firing mechanism of the lancing device. A lancet is movably received by a cartridge, which is removably received by the lancing device. The lancet is movable between a first position in which a penetrating member connected to the lancet is not exposed and a second position in which the penetrating member is exposed outside of the cartridge for lancing a site. A spring is connected to the cartridge to return the lancet to the first position after the site is lanced.

A method of lancing using a lancing device in accordance with aspects of the present invention includes installing a cartridge housing a movable lancet in the lancing device. The lancet is used to lance a site. The cartridge is removed from the lancing device, and the used lancet in the cartridge is replaced with a new lancet. Alternatively, a new cartridge containing a new lancet can be installed.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which.

Throughout the drawings, like reference numbers will be understood to refer to like parts, components and structures.

DETAILED DESCRIPTION OF THE EXEMPLARY EMBODIMENTS

Figure 7:
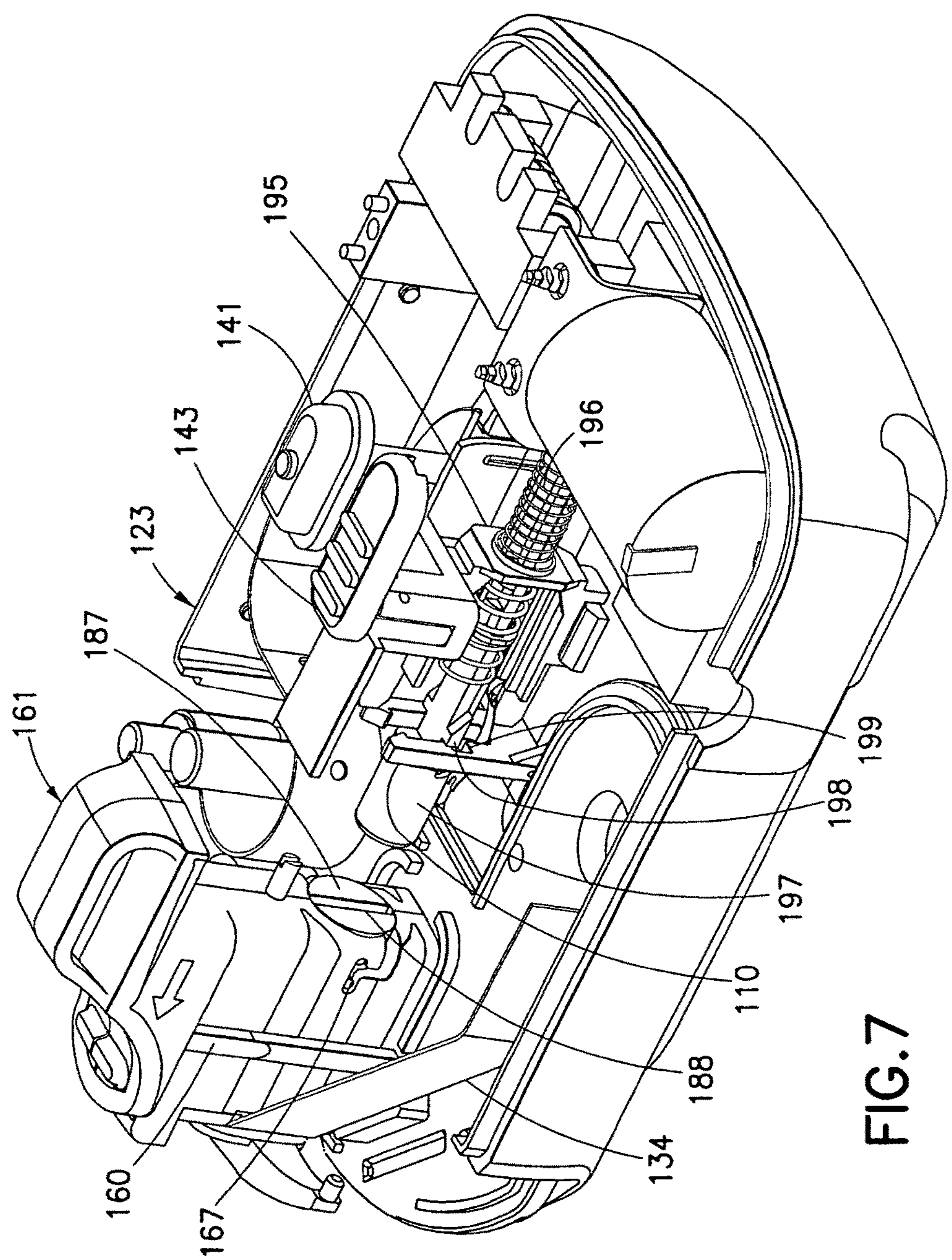
FIG. 7 is a perspective view of the lancing device of FIG. 6.
Figure 8:
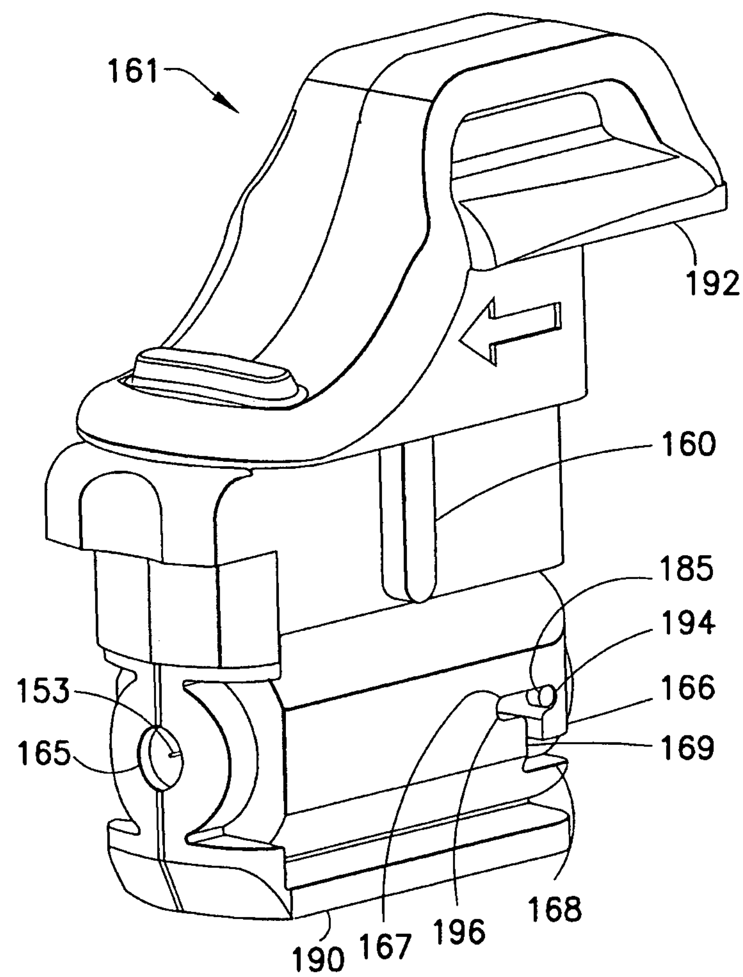
FIG. 8 is a perspective view of a lancing cartridge assembly installable in the lancing device of FIG. 1 in which the lancet is disposed in a first position.

The exemplary embodiments of the present invention, as shown in FIGS. 1-17, provide a lancing device 121 that substantially reduces wobble associated with a, lancet not directly connected to a firing mechanism. A lancet 151, as shown in FIGS. 5 and 11, is movably received by a cartridge 161, which is removably received by the lancing device 121. Alternatively, the lancet 151 can be removably received by the cartridge 161. The lancet 151 is movable between a first position, as shown in FIG. 4, in which a penetrating member 153, such as a stylet or a hollow or solid body needle, connected to the lancet 151 is unexposed, and a second position, as shown in FIG. 8, in which the penetrating member 153 is exposed outside of the cartridge 161 for lancing a site. A spring 171 is connected to the cartridge 161 to return the lancet 151 to the first position after the site is lanced.

Figure 1:
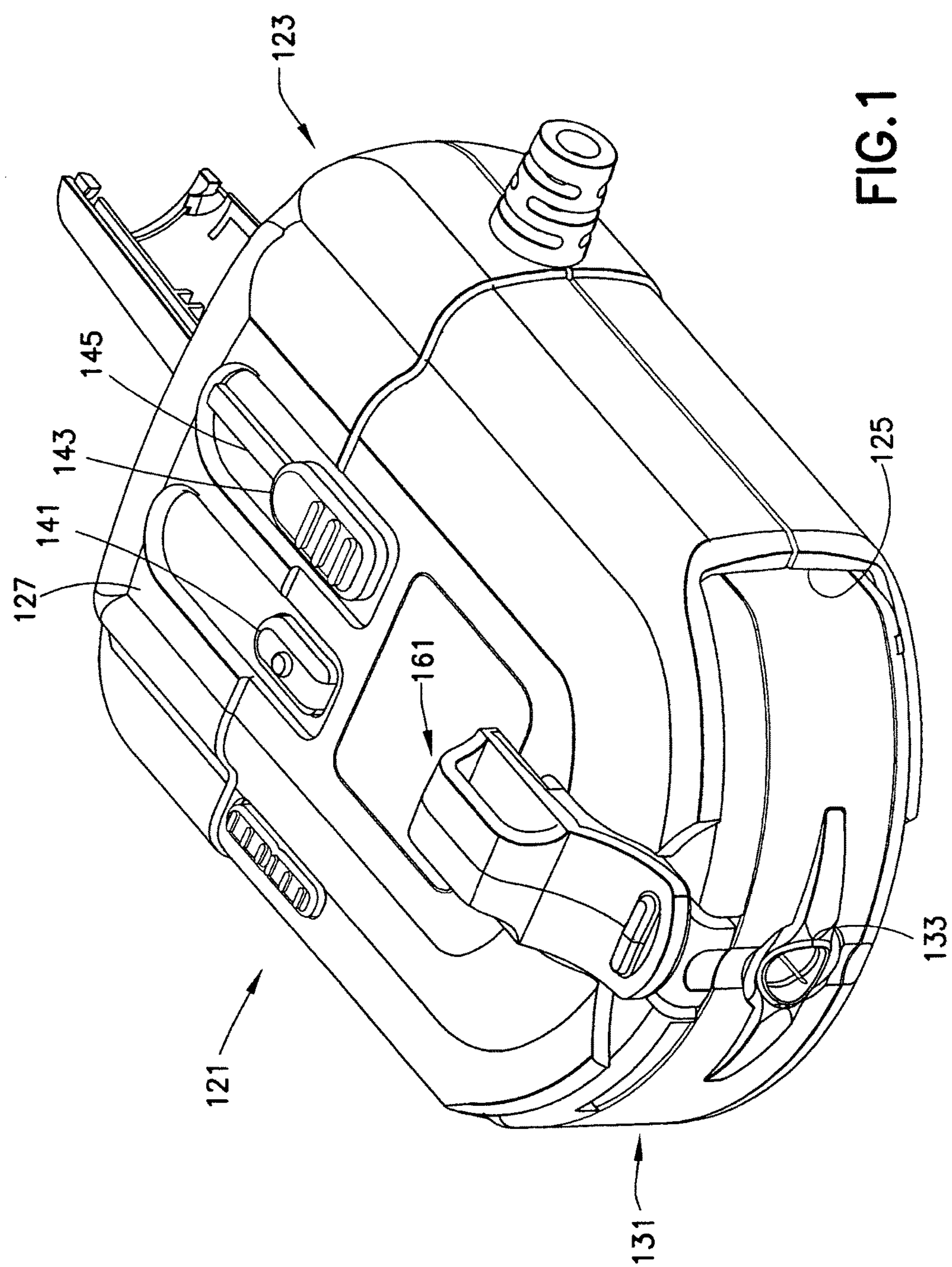
FIG. 1 is a perspective view of a lancing device according to an exemplary embodiment of the present invention.
Figure 2:
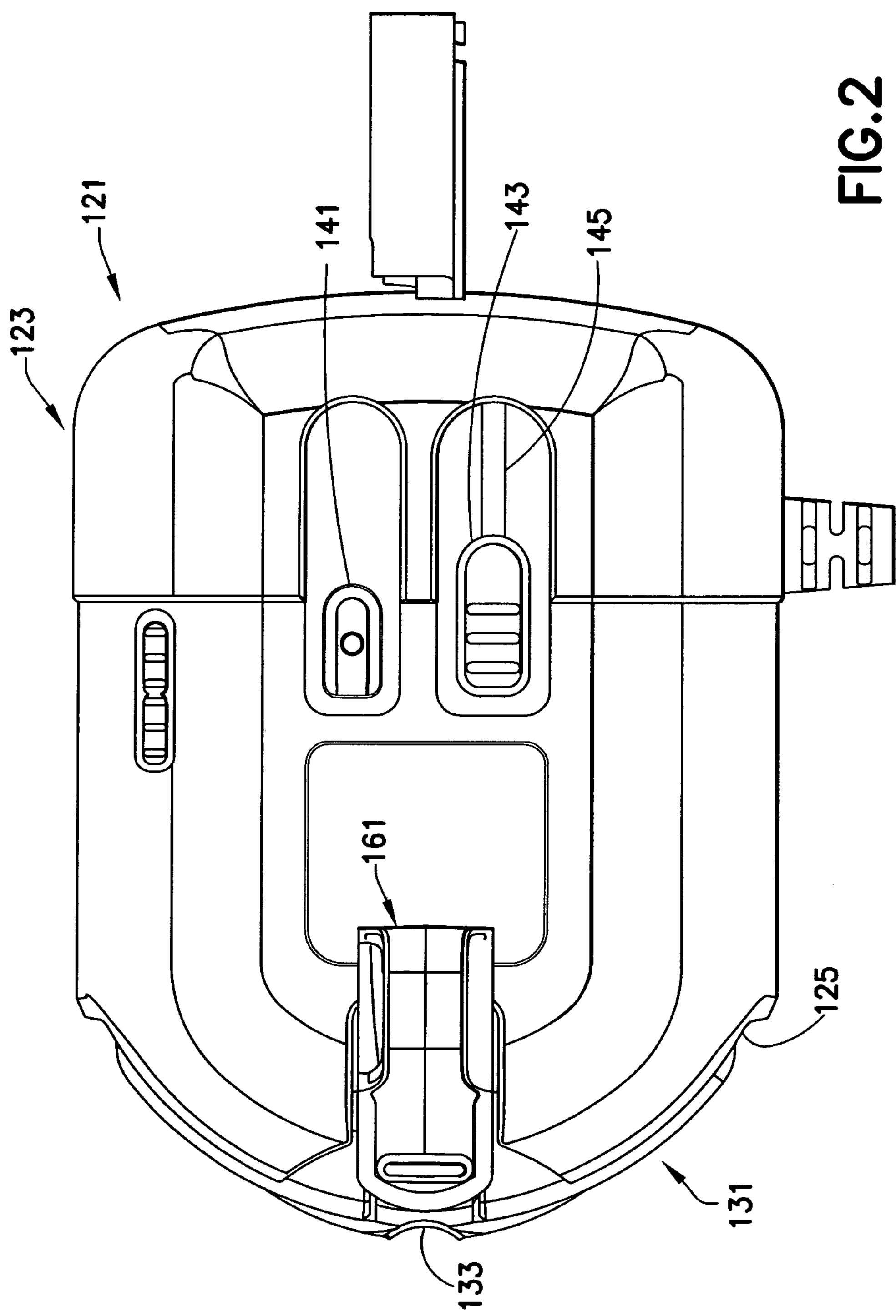
FIG. 2 is a top plan view of the lancing device of FIG. 1.
Figure 3:
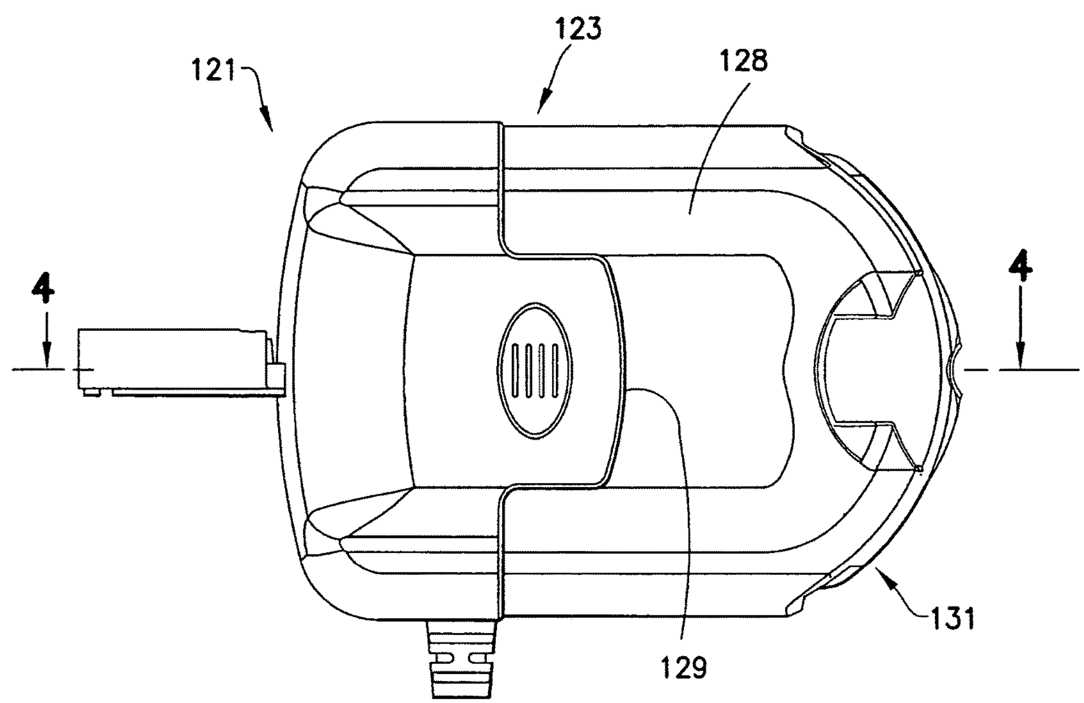
FIG. 3 is a bottom plan view of the lancing device of FIG. 1.
Figure 4:
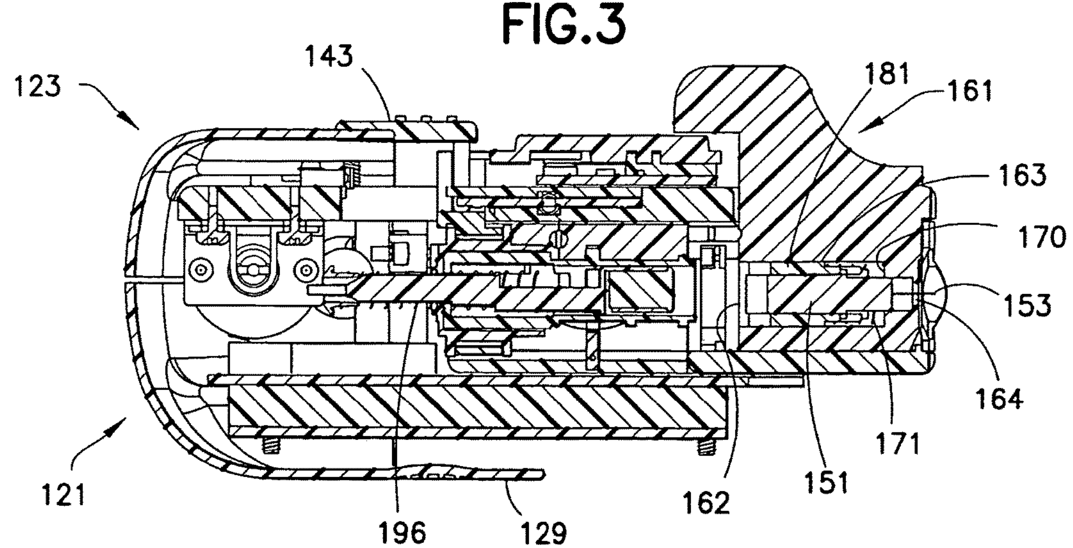
FIG. 4 is an elevational view in cross-section of the lancing device taken along line 4-4 of FIG. 3.
Figure 5:
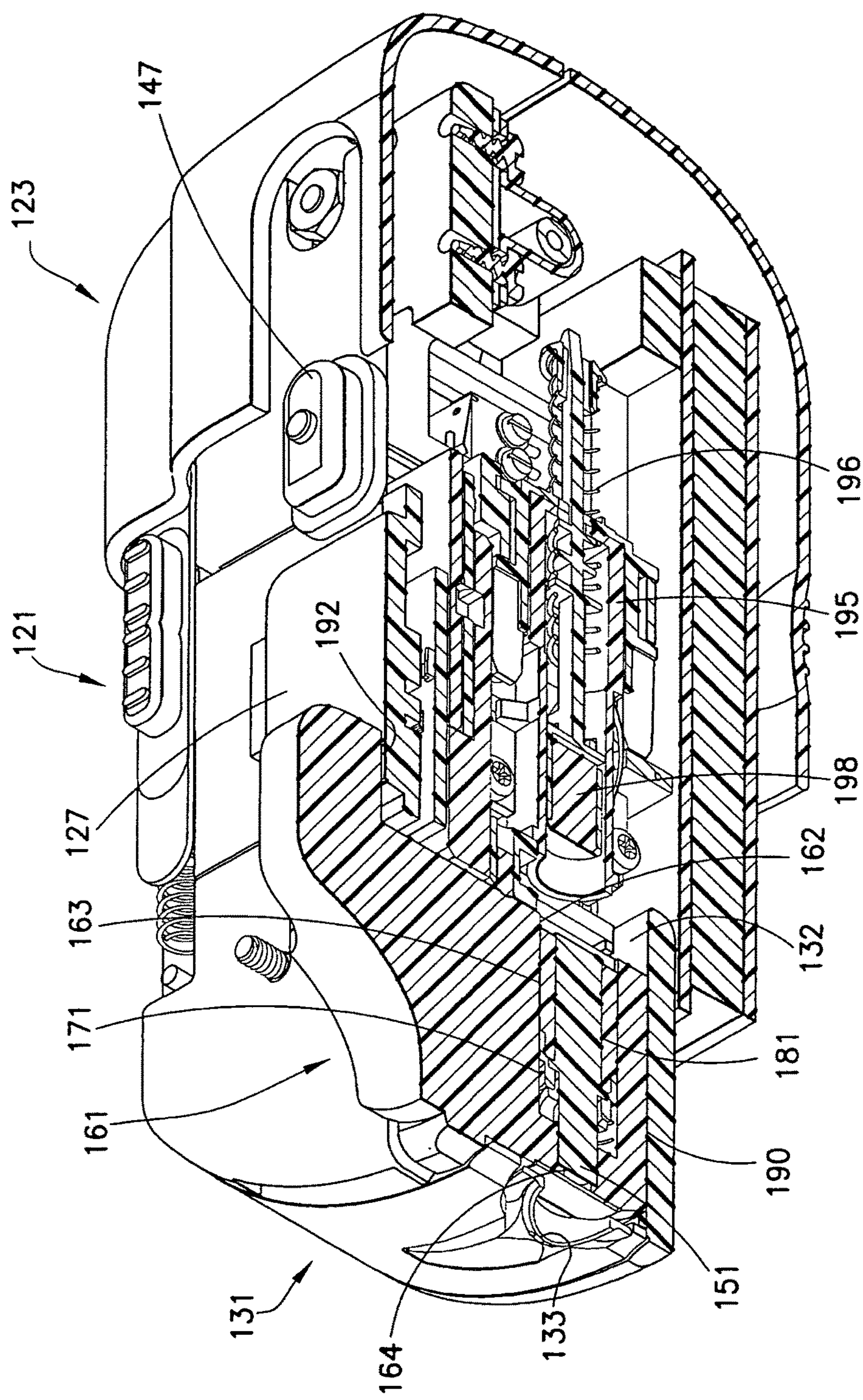
FIG. 5 is a perspective view in cross-section of the lancing device of FIG. 1.

A lancing device 121, as shown in FIGS. 1-7 and 10, has a housing 123 in which an aperture 125 is formed. An upper surface 127 of the lancing device has an arming button 143 and a firing button 141 for arming and firing the lancet 151, respectively, as shown in FIGS. 1 and 2. A finger grip 129 is connected to the housing 123, as shown in FIGS. 3 and 4, and extends in a direction substantially parallel to a rear surface 128 of the lancing device 121 to facilitate proper alignment of the lancing device.

Figure 6:
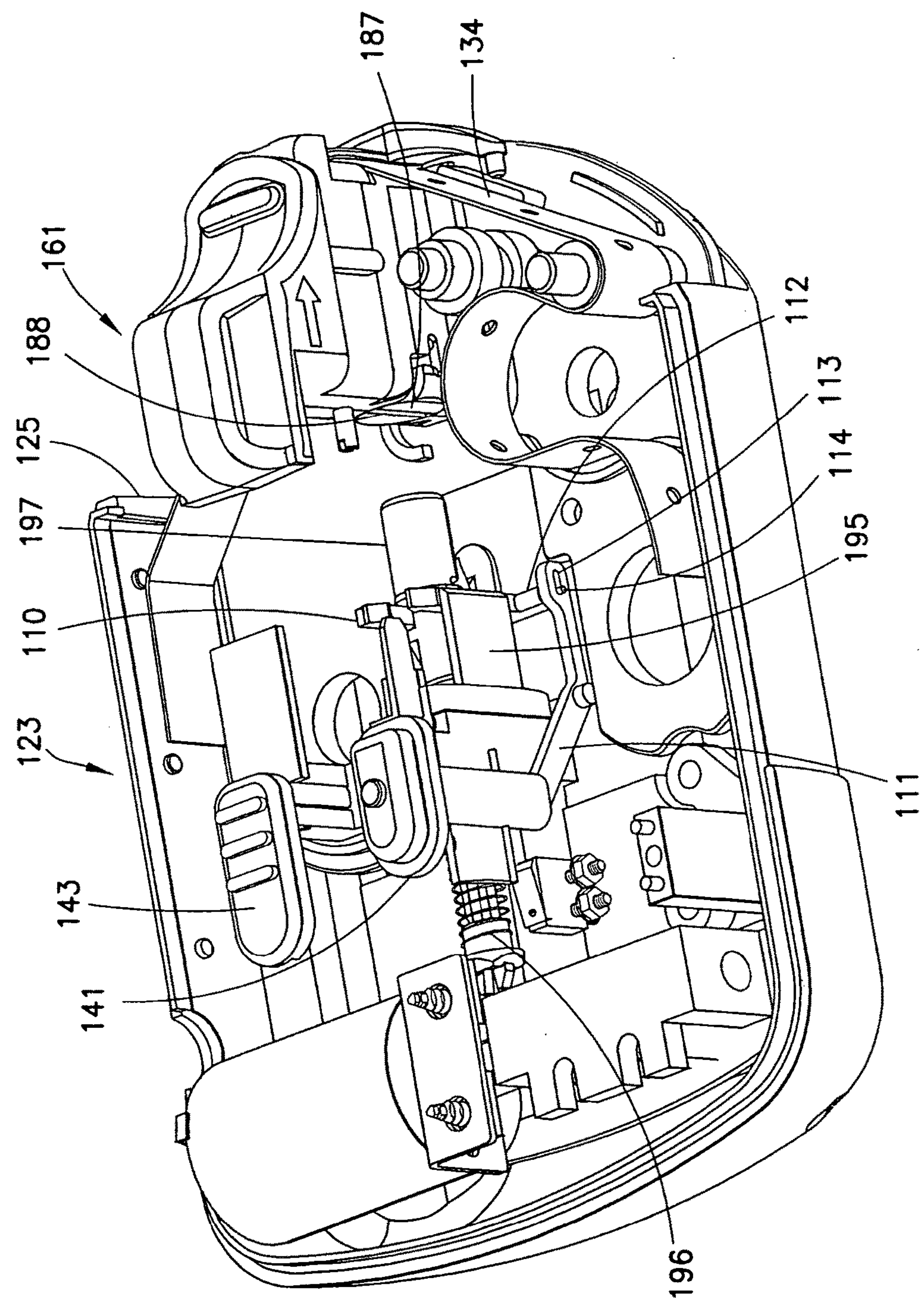
FIG. 6 is a top plan view of the lancing device of FIG. 1 with the cover removed to show the firing mechanism.

A reel housing 131 is removably disposed in the housing aperture 125, as shown in FIG. 1. An opening 133 in the reel housing 131 allows the penetrating member 153 of the lancet 151 to pass therethrough when lancing a site. A sensing strip 134, as shown in FIGS. 6 and 7, is disposed in the reel housing 131 and moves from a lancing position to an acquisition position when the lancet 151 is fired to lance a site. In the acquisition position, blood is drawn from the lanced site to fill a capillary of the sensing strip 134. When the capillary is filled, the sensing strip 134 further advances and the gathered information is then processed and the desired output is generated. The sensing strip 134 then advances to the next lancing position. A detailed description of such capillary technology is found in U.S. Pat. No. 7,192,405, which is hereby incorporated by reference in its entirety.

A cartridge 161 has a bore 163 for receiving the sleeve 181 and lancet 151, as shown in FIGS. 4 and 5. An outer diameter of the bore 163 at a second end 162 is greater than a diameter of the bore 163 at a first end 164, as shown in FIG. 4. The second end 162 of the bore 163 has a larger diameter to facilitate inserting and removing the sleeve 181 and lancet 151. The smaller diameter of the first end 164 of the bore 163 prevents the sleeve 181 and lancet 151 from being pushed out of the cartridge when struck by the firing mechanism of the lancing device 121.

A spring 171 has a first end 173 engaging the lancet flange 155 and a second end engaging the cartridge 161, as shown in FIGS. 4 and 5. The spring 171 biases the lancet 151 to the first position, as shown in FIG. 8, in which the penetrating member 153 is not exposed outside of the lancing device 121.

A sleeve 181 has an opening 183 at a first end 182 that receives the second body portion 158 of the lancet 151, as shown in FIG. 11. The lancet flange 155 abuts the first end 182 and prevents further insertion of the lancet in the sleeve 181. At least one protrusion 185 extends outwardly from an outer surface 184 of the sleeve 181. A groove 188 is formed in the second end 187 of the sleeve 181.

Figure 9:
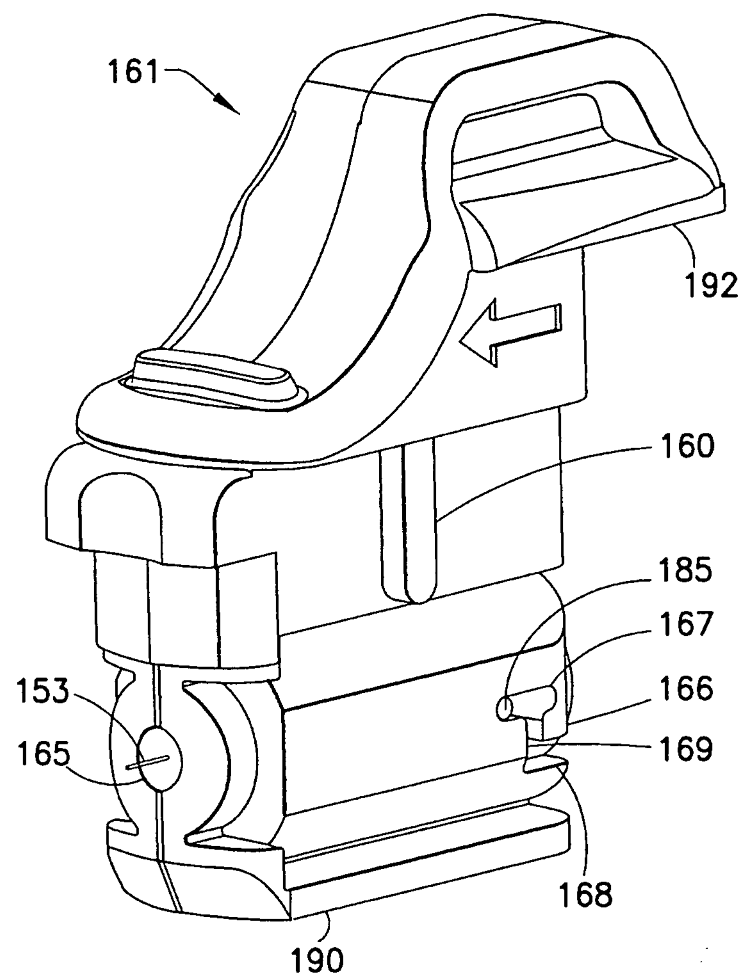
FIG. 9 is a perspective view of the lancing cartridge assembly of FIG. 8 in which the lancet is disposed in a second position.

A slot 167 extends in a direction parallel to the direction in which the lancet 151 moves, as shown in FIGS. 8, 9 and 11. An entrance slot 168 extends from an outer surface 166 of the cartridge 161 proximal the second end 162 of the bore 163 to a connecting slot 169, which connects the entrance slot 168 to the slot 167. The sleeve protrusion 185 is moved through the entrance slot 168 when inserting the sleeve 181 in the bore 163. When the end of the entrance slot 168 is reached, a tool is inserted in the groove 188 in the second end 187 of the sleeve 181 to rotate the sleeve. The rotation causes the protrusion 185 to move through the connecting slot 169 to the slot 167. The spring 171 then biases the sleeve 181 rearwardly, by pushing the protrusion 185 rearwardly in the slot 167, thereby securing the sleeve 181 within the bore 163 of the cartridge 161.

The lancet 151 has an outer surface 152 around which a flange 155 extends, as shown in FIG. 11. A first body portion 156 extends from the flange 155 to a first end 157 of the lancet 151. A penetrating member 153 extends outwardly from the first end 157 of the lancet 151. A second body 158 portion extends from the flange 155 to a second end 159 of the lancet 151.

Assembly and Operation

Figure 10:
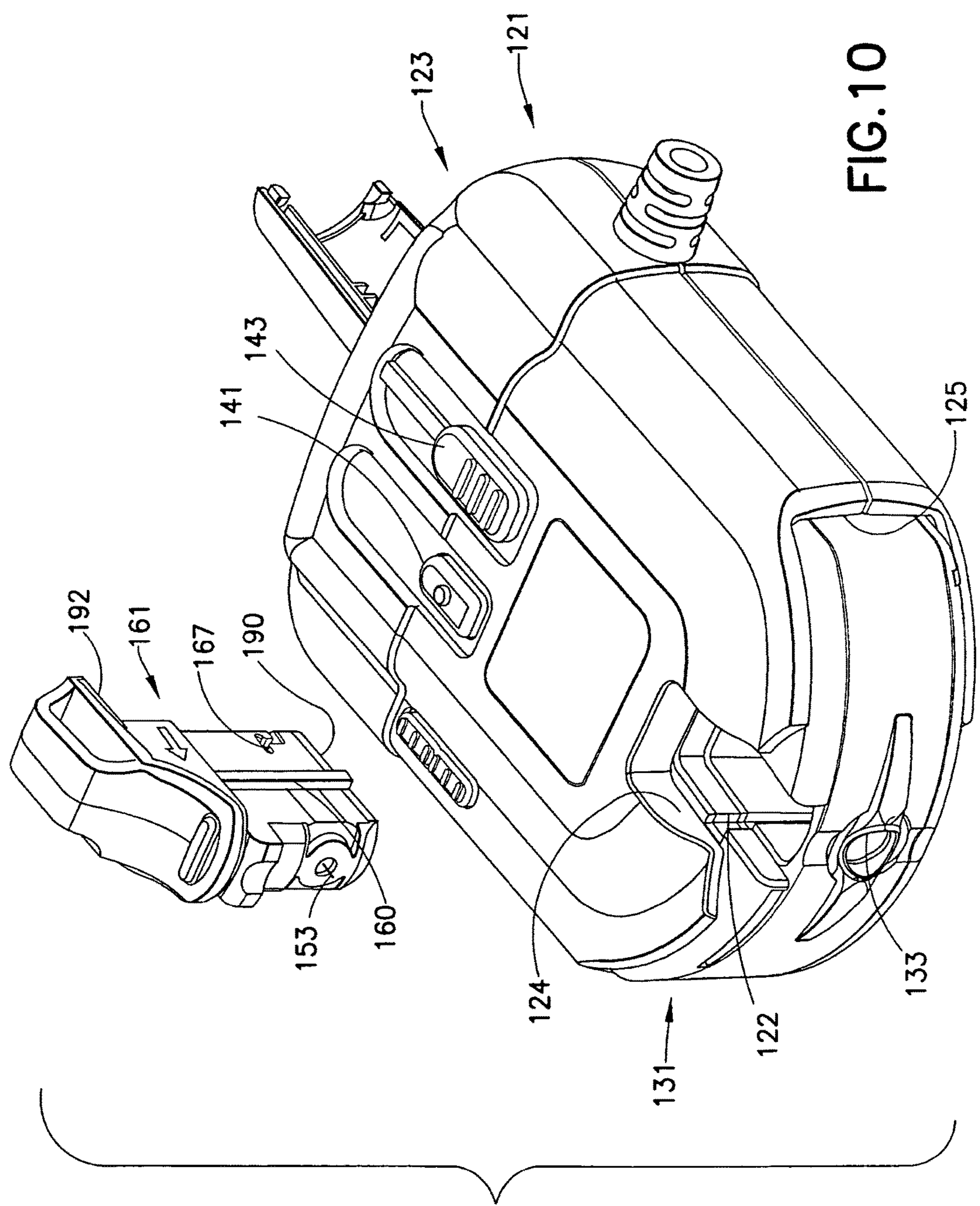
FIG. 10 is a perspective view of the lancing cartridge prior to being connected to the lancing device.
Figure 11:
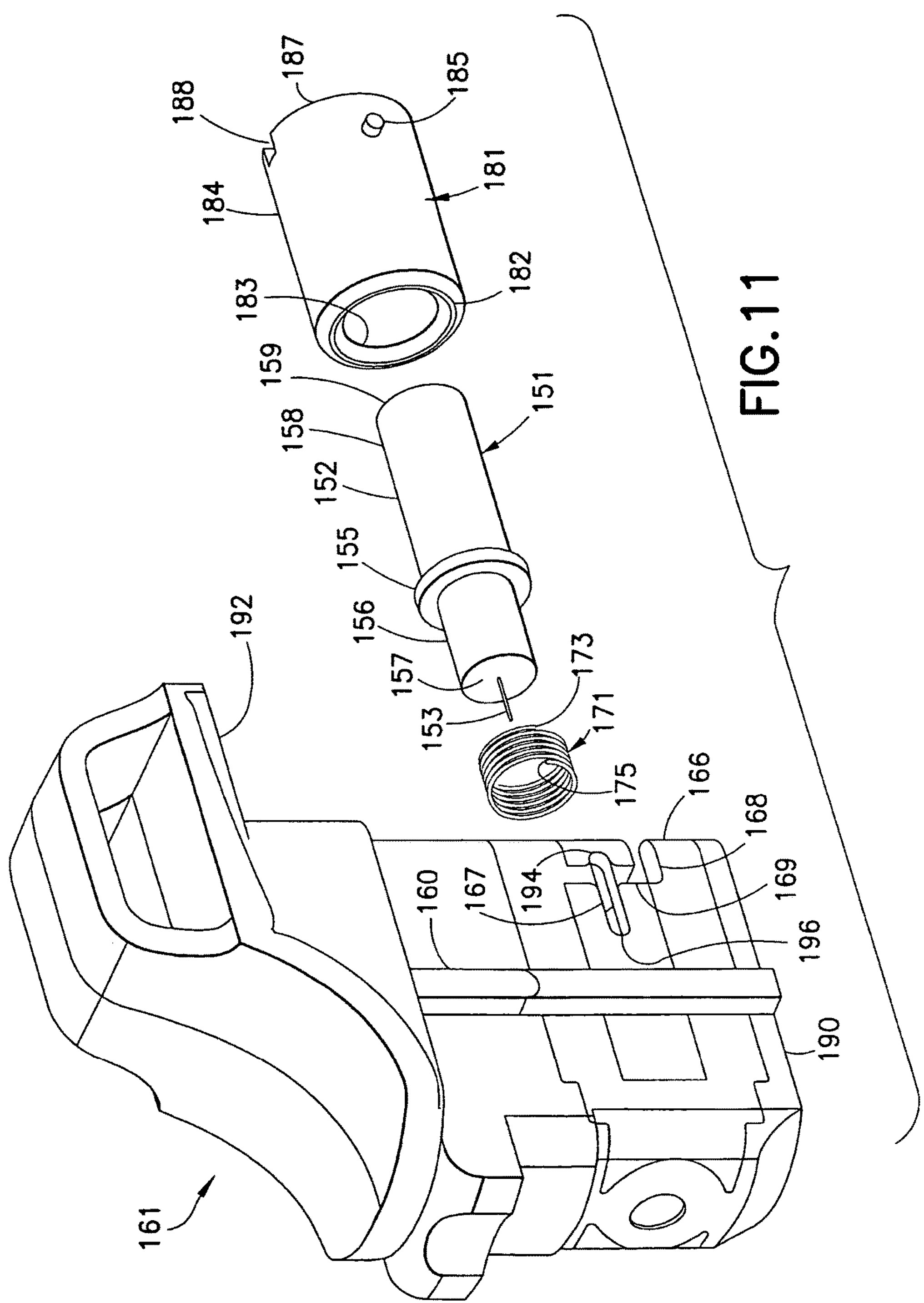
FIG. 11 is an exploded perspective view of the lancing cartridge assembly of FIG. 8.

As shown in FIG. 10, the reel housing 131 is inserted in the housing aperture 125. A cavity 124 is formed between housing 123 and the reel housing 131 to receive the cartridge 161. Grooves 122 are formed in the cavity 124 to receive rails 160 of the cartridge 161.

To prepare the cartridge 161 for insertion, the spring 171 is disposed on the first body portion 156 of the lancet 151, such that the first end 173 of the spring 171 abuts the lancet flange 155. The sleeve 181 is inserted on the second body portion 158 of the lancet 151 such that the first end 182 of the sleeve abuts the lancet flange 155. The lancet assembly is then inserted in the cartridge bore 163 such that the sleeve protrusion 185 enters the entrance slot 168. When the sleeve protrusion 185 abuts the end of the entrance slot 168, the sleeve 181 is rotated, such as by inserting a tool, such as a screwdriver, into the sleeve slot 188, such that the protrusion 185 passes through the connecting slot 169 and into the slot 167. The spring 171 then biases the lancet 151 and sleeve 181 rearwardly such that the protrusion 185 moves to the rear end 194 of the slot, as shown in FIG. 8. The second end 175 of the spring 171 abuts an inner surface 170 of the bore, as shown in FIG. 4, thereby biasing the lancet 151 and sleeve 181 rearwardly. The protrusion 185 being received by the slot 167 also locks the lancet 151 and sleeve 181 in the cartridge 161.

The cartridge 161 is then inserted in the cavity 124, as shown in FIGS. 1, 5 and 7. The cartridge rails 160 engage the grooves 122 to align the cartridge in the cavity 124. When the cartridge 161 is fully inserted in the cavity 124, a bottom surface 190 of the cartridge 161 abuts a surface 132 of the reel housing 131, as shown in FIG. 5, and a shoulder 192 of the cartridge 161 abuts an upper surface 127 of the housing 123. The lancet 151 is in the first position, as shown in FIG. 8, prior to lancing.

When a site is to be lanced, the arming button 143 is slid rearwardly on the track 145 to arm the firing mechanism. A carriage 195 is connected to the arming button 143, that slides rearwardly with the arming button 143, as shown in FIG. 7. A firing spring 196 is disposed on a plunger rod 197 that is movably connected to the carriage 195. Rearward movement of the carriage 195 causes the spring 196 to compress. A shoulder 198 on the plunger rod 197 abuts a wall 110 of the carriage 195 that moves the plunger rod 197 and spring 196 rearwardly with the carriage 195.

The firing button 141 is depressed to fire the plunger rod 197 into the second end 187 of the sleeve 181, as shown in FIGS. 5 and 6. A connecting arm 111 connects the firing button 141 to the carriage wall 110. A rod 112 extends between the carriage 195 and the connecting arm 111. A slot 113 in the connecting arm 111 receives an end 114 of the rod 112. When the lancing device 121 is armed and a site is to be lanced, the opening 133 (FIG. 1) is positioned at the lancing site. The firing button 141 is depressed, thereby causing the connecting arm 111 to raise the rod 112, which in turn raises the carriage wall 110. When the wall 110 is lifted, the wall opening 199 (FIG. 7) is aligned with the plunger rod shoulder 198 such that the wall no longer prevents movement of the plunger rod 197. The compressed spring 196 moves the plunger rod 197 forward, such that the plunger rod strikes the second end 187 of the sleeve 181.

The forward movement of the sleeve 181 moves the lancet 151 forward by the engagement between the first end 182 of the sleeve and the lancet flange 155. The movement of the sleeve 181 is guided by the protrusion 185 moving through the slot 167 from the first position (FIG. 8) to the second position (FIG. 9). The lancet 151 moves toward the first end 164 of the bore, such that the lancet penetrating member 153 passes through the opening 133 and lances the site. The spring 171 then expands back to its original shape, thereby retracting the penetrating member 153 to an unexposed position within the lancing device housing 123 to prevent accidental sticks from the penetrating member. The sleeve 181 substantially prevents wobble of the lancet 151 during the lancing procedure by providing a straight and smooth path for accurate movement of the lancet.

The cartridge 161 is lifted upwardly out of the cavity, as shown in FIG. 10, to remove the cartridge from the lancing device 123. The direction in which the cartridge 161 is removed is substantially perpendicular to the direction in which the lancet 151 moves during a lancing procedure. Additionally, the cartridge 161 is not directly connected to the firing mechanism such that the cartridge is simply pulled out of the housing 123 without having to manipulate any other components. The groove 188 on the sleeve is rotated to slide the protrusion 185 out of the slots 167, 169 and 168, respectively, such that the sleeve and lancet can be removed from the cartridge. The used lancet 151 is replaced with a new lancet, and the cartridge 161 and lancing device 121 can be easily reassembled as described above. Alternatively, the entire cartridge 161 can be removed and properly disposed of such that the lancet 151 does not have to be handled after use. A new cartridge 161 can be inserted in the lancing device 123, such that the lancet 151 is also not handled during installation.

Additional Exemplary Embodiments of the Lancing Cartridge

The following exemplary embodiments of lancing cartridges are adapted to be receivable in the cavity 124 of the lancing device 121, as shown in FIG. 10. The lancet 151 is substantially identical in each of the following exemplary embodiments.

As shown in FIG. 10, a lancet cartridge assembly 201 in accordance with a second exemplary embodiment of the present invention includes a lancet 151 movably disposed in a cartridge 221. The lancet 151 has a first end 157 and a second end 159. A penetrating member 153 extends outwardly from the first end 157. A flange 155 extends outwardly from an outer surface 152 of the lancet 151. Preferably, the flange 155 is unitarily formed with the lancet 211 as a one-piece assembly.

The cartridge 221 has a through bore 223 through which the lancet 151 moves when struck by a firing mechanism of the lancing device. An accommodating portion 225 of the through bore 223 has a larger diameter than the rest of the through bore to accommodate the flange 155 of the lancet 151. The accommodating portion 225 has a first end 227 and a second end 229 that limits movement of the lancet 151. A spring 231 is connected between the lancet flange 155 and the second end 229 of the accommodating portion 225.

Figure 12:
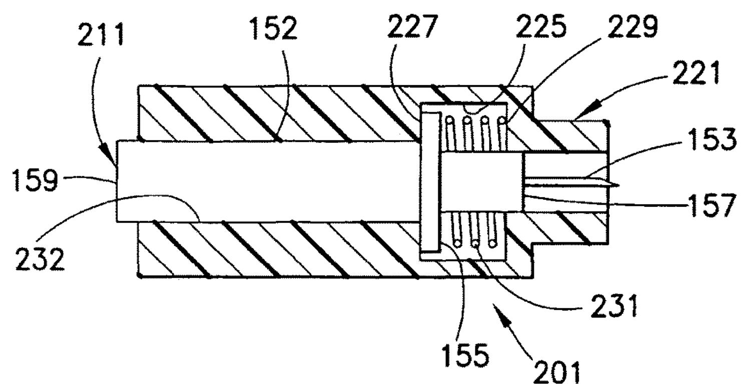
FIG. 12 is an elevational view in partial cross-section of a lancing cartridge assembly according to a second exemplary embodiment of the present invention.

The lancet 151 is movable between a first position, as shown in FIG. 12, in which the penetrating member 153 is disposed within the cartridge 221 and is unexposed with respect to the lancing device 121 in which the cartridge is disposed, and a second position in which the penetrating member exits the cartridge to lance a site. In the first position, the spring 231 urges the lancet flange 155 toward the first end 227 of the accommodating portion 225 of the cartridge 221. When the second end 159 of the lancet 151 is struck by the firing mechanism, the movement of the lancet 151 (to the right as shown in FIG. 12) compresses the spring 241, such that once the site has been lanced the spring returns the lancet to the first position. The second end 229 of the accommodating portion 225 limits travel of the struck lancet 151. The cartridge 221 is fixed in the lancing device 121 such that the cartridge is prevented from moving when the lancet is struck by the firing mechanism. The cartridge bore 223 substantially prevents wobble of the lancet 151 during the lancing procedure by providing a straight and smooth path for accurate movement of the lancet.

Figure 13:
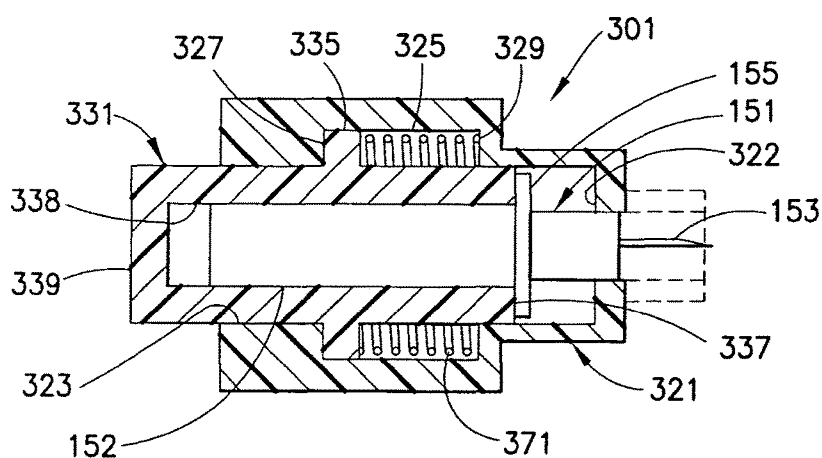
FIG. 13 is an elevational view in partial cross section of a lancing cartridge assembly according to a third exemplary embodiment of the present invention.

As shown in FIG. 13, a lancet cartridge assembly 301 in accordance with a third exemplary embodiment of the present invention includes a lancet 151 movably disposed in a cartridge 321. The cartridge 321 has a through bore 323 through which the lancet 151 moves when a sleeve 331 is struck by a firing mechanism of the lancing device 121. An accommodating portion 325 of the through bore 323 has a larger diameter than the rest of the through bore to accommodate the lancet flange 155. The accommodating portion 325 has a first end 327 and a second end 329 that limits movement of a flange 335 of a sleeve 331. A spring 371 is connected between the sleeve flange 335 and the second end 329 of the accommodating portion 325. A bore 338 in the sleeve 331 receives the lancet 151, such that a first end 337 of the sleeve abuts the lancet flange 155. Preferably, an interference fit is created between the sleeve 331 and the lancet 151 such that the lancet moves with the sleeve.

The lancet 151 is moved between a first position, as shown in FIG. 13, in which the penetrating member 153 is disposed within the cartridge 321, and a second position in which the penetrating member exits the cartridge 321 to lance a site. In the first position, the spring 371 urges the sleeve flange 335 toward the first end 327 of the accommodating portion 325 of the cartridge 321. When the second end 339 of the sleeve 331 is struck by the firing mechanism, the sleeve 331 is moved to the right as shown in FIG. 13, which also compresses the spring 371, such that once the site has been lanced the spring returns the sleeve and the lancet to the first position. The second end 329 of the accommodating portion 325 limits travel of the struck sleeve 331. An inner surface 322 of the cartridge 321 limits travel of the lancet 151. The cartridge 321 is fixed in the lancing device 121 such that the cartridge is prevented from moving when the lancet is struck by the firing mechanism. The cartridge bore 323 and sleeve 331 substantially prevent wobble of the lancet 151 during the lancing procedure by providing a straight and smooth path for accurate movement of the lancet.

Figure 14:
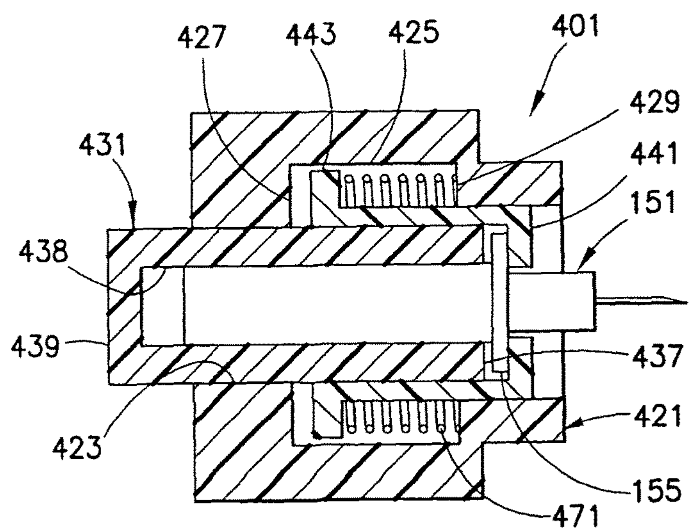
FIG. 14 is an elevational view in partial cross section of a lancing cartridge assembly according to a fourth exemplary embodiment of the present invention.

As shown in FIG. 14, a lancet cartridge assembly 401 in accordance with a fourth exemplary embodiment of the present invention includes a lancet 151 movably disposed in a cartridge 421. The cartridge 421 has a through bore 423 through which the lancet 151 moves when a first sleeve 431 is struck by a firing mechanism of the lancing device 121. An accommodating portion 425 of the through bore 423 has a larger diameter than the rest of the through bore to accommodate a first flange 443 of a second sleeve 441. The accommodating portion 425 has a first end 427 and a second end 429 that limits movement of the first flange 443 of the second sleeve 431. A spring 471 is connected between the second sleeve flange 443 and the second end 429 of the accommodating portion 425. A bore 438 in the first sleeve 431 receives the lancet 151, such that a first end 437 of the first sleeve abuts the lancet flange 155. Preferably, an interference fit is created between the first sleeve 431 and the lancet 151 such that the lancet moves with the first sleeve. The second sleeve 441 has a second flange 445 engaging an opposite side of the lancet flange 155, such that the second sleeve moves with the lancet and the first flange.

The lancet 151 is moved between a first position, as shown in FIG. 14, in which the penetrating member 153 is disposed within the cartridge 421, and a second position in which the penetrating member exits the cartridge 421 to lance a site. In the first position, the spring 471 urges the second sleeve first flange 443 toward the first end 427 of the accommodating portion 425 of the cartridge 421, thereby also urging the lancet 151 and first sleeve 431 rearwardly. When a second end 439 of the first sleeve 431 is struck by the firing mechanism, the sleeve 431 is moved to the right as shown in FIG. 14, which also compresses the spring 471, such that once the site has been lanced the spring returns the second sleeve, and thus the lancet 151 and the first sleeve 431, to the first position. The second end 429 of the accommodating portion 425 limits travel of the struck first flange 443 of the second sleeve 441. The cartridge 421 is fixed in the lancing device 121 such that the cartridge is prevented from moving when the lancet is struck by the firing mechanism. The cartridge bore 423 and the first and second sleeves 431 and 441 substantially prevent wobble of the lancet 151 during the lancing procedure by providing a straight and smooth path for accurate movement of the lancet.

Figure 15:
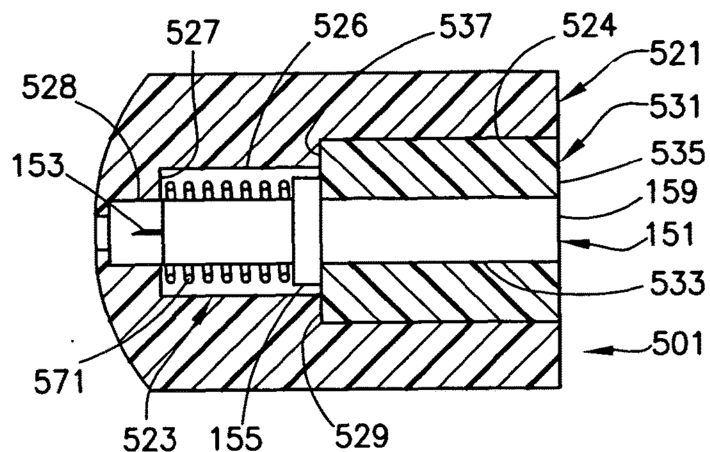
FIG. 15 is an elevational view in partial cross section of a lancing cartridge assembly according to a fifth exemplary embodiment of the present invention.

As shown in FIG. 15, a lancet cartridge assembly 501 in accordance with a fifth exemplary embodiment of the present invention includes a lancet 151 movably disposed in a cartridge 521. The cartridge 521 has a through bore 523 through which the lancet 151 moves when struck by a firing mechanism of the lancing device 121. The through bore 523 has first, second and third portions 524, 526 and 528, each of which has a progressively smaller diameter. The first portion 524 receives a sleeve 531. Preferably, an interference fit is created between the first portion 524 and the sleeve 531. A bore 533 of the sleeve 531 movably receives the portion of the lancet 151 rearward of the flange 155, such that the lancet flange abuts a second end 537 of the sleeve 531. The lancet flange 155 is movably received in the second portion 526 of the bore 523. A first shoulder 527 between the second and third portions 526 and 528 of the bore 523 limits movement of the lancet flange 155. A spring 571 is connected between the lancet flange 155 and the shoulder 527.

Figure 16:
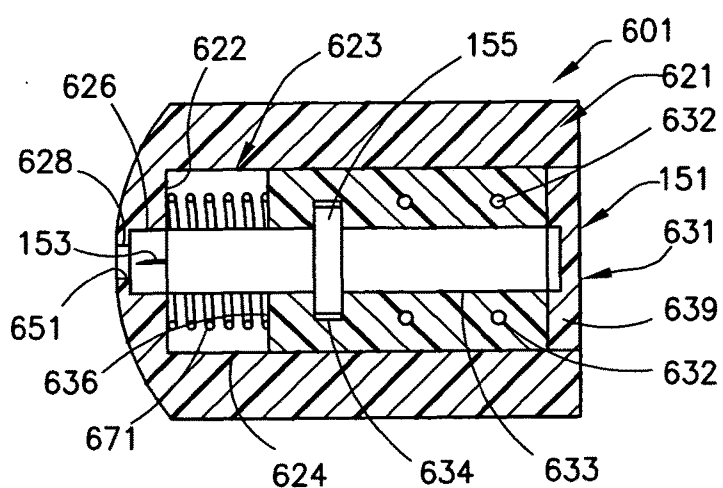
FIG. 16 is an elevational view in cross section of a lancing cartridge assembly according to a sixth exemplary embodiment of the present invention.

The lancet 151 is moved between a first position, as shown in FIG. 16, in which the penetrating member 153 is disposed within the cartridge 521, and a second position in which the penetrating member exits the cartridge 521 to lance a site. In the first position, the spring 571 urges the lancet flange 155 rearwardly toward the second end 537 of the sleeve 531. The first end 535 of the sleeve 531 and the second end 159 of the lancet 151 are struck by the firing mechanism. The sleeve 531 is prevented from moving by a second shoulder 529 between the first and second portions 524 and 526 of the bore 523. The lancet 151 is moved to the left as shown in FIG. 15, which also compresses the spring 571, such that once the site has been lanced the spring returns the lancet to the first position. The first shoulder 527 limits travel of the struck lancet 151 by having a diameter smaller than that of the lancet flange 155. The cartridge 521 is fixed in the lancing device 121 such that the cartridge is prevented from moving when the lancet is struck by the firing mechanism. The cartridge bore 523 and sleeve 531 substantially prevent wobble of the lancet 151 during the lancing procedure by providing a straight and smooth path for accurate movement of the lancet.

As shown in FIG. 16, a lancet cartridge assembly 601 in accordance with a sixth exemplary embodiment of the present invention includes a lancet 151 movably disposed in a cartridge 621. The cartridge 621 has a through bore 623 through which the lancet 151 and sleeve 631 move when struck by a firing mechanism of the lancing device 121. The through bore 623 has first, second and third portions 624, 626 and 628, each of which has a progressively smaller diameter. The first portion 624 receives a sleeve 631 and the lancet 151. A bore 633 of the sleeve 631 fixedly receives the lancet 151. An accommodating portion 634 of the bore 633 receives the lancet flange 155. The sleeve 631 may have first and second body portions that have snap fasteners 632 to snap the first and second body portions together, thereby facilitating disposing the lancet 151 within the sleeve 631. A cap 639 may be threaded onto the first and second body portions.

The second portion 626 of the bore 623 is sized to receive a portion of the lancet 151 forward of the flange 155. The diameter of the second portion 626 of the bore 623 is smaller than that of the sleeve 631, thereby preventing the sleeve from passing therethrough. A spring 671 is connected between a first end 636 of the sleeve 631 and a shoulder 622 between the first and second portions 624 and 626 of the bore 623.

The lancet 151 is moved between a first position, as shown in FIG. 16, in which the penetrating member 153 is disposed within the cartridge 621, and a second position in which the penetrating member exits the cartridge 621 to lance a site. In the first position, the spring 671 urges the sleeve 631, and thus the lancet 151, away from the cartridge opening 651. When the cap 639 of the sleeve 631 is struck by the firing mechanism, the sleeve 631 is moved to the left as shown in FIG. 16, which also compresses the spring 671, such that once the site has been lanced the spring returns the sleeve and the lancet to the first position. The shoulder 622 of the bore 623 limits travel of the struck sleeve 631. The cartridge 621 is fixed in the lancing device 121 such that the cartridge is prevented from moving when the lancet is struck by the firing mechanism. The cartridge bore 623 and sleeve 631 substantially prevent wobble of the lancet 151 during the lancing procedure by providing a straight and smooth path for accurate movement of the lancet.

Figure 17:
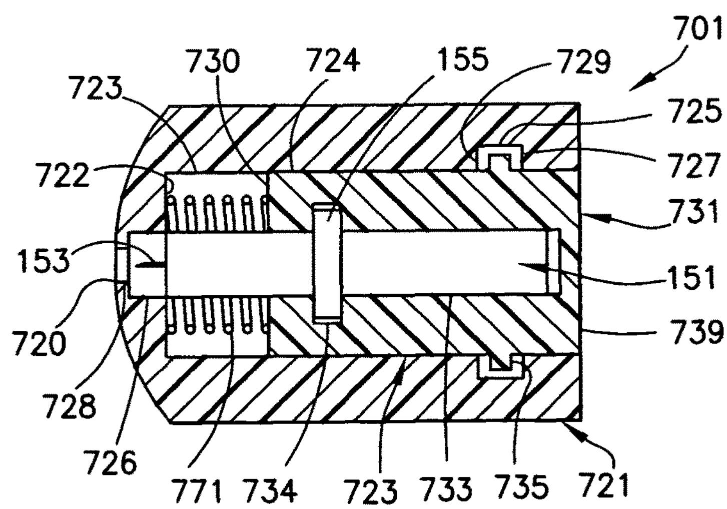
FIG. 17 is an elevational view in cross section of a lancing cartridge assembly according to a seventh exemplary embodiment of the present invention.

As shown in FIG. 17, a lancet cartridge assembly 301 in accordance with a seventh exemplary embodiment of the present invention includes a lancet 151 movably disposed in a cartridge 721. The cartridge 721 has a through bore 723 through which the lancet 151 and sleeve 731 move when struck by a firing mechanism of the lancing device 121. The through bore 723 has first, second and third portions 724, 726 and 728, each of which has a progressively smaller diameter. The first portion 724 receives the sleeve 731 and the lancet 151. An opening 733 of the sleeve 731 fixedly receives the lancet 151. An accommodating portion 734 of the opening 733 receives the lancet flange 155. The cartridge 721 has a through bore 723 through which the lancet 151 and sleeve 731 move when a sleeve 731 is struck by a firing mechanism of the lancing device 121. An accommodating portion 725 of the through bore 723 has a larger diameter than the rest of the through bore to accommodate a flange 735 of the sleeve 731. The accommodating portion 725 has a first end 727 and a second end 729 that limits movement of the sleeve flange 735. A shoulder 722 between the first and second portions 724 and 726 limits forward travel of the sleeve 731 by having a diameter smaller than the diameter of the first end 730 of the sleeve 731. A spring 771 is connected between the first end 730 of the sleeve 731 and the shoulder 722 of the bore 723.

The lancet 151 is moved between a first position, as shown in FIG. 17, in which the penetrating member 153 is disposed within the cartridge 721, and a second position in which the penetrating member exits the cartridge 721 through an opening 720 to lance a site. In the first position, the spring 771 urges the sleeve flange 735 toward the first end 727 of the accommodating portion 725 of the cartridge bore 723. When the second end 739 of the sleeve 731 is struck by the firing mechanism, the sleeve 731 is moved to the left as shown in FIG. 17, which also compresses the spring 771, such that once the site has been lanced the spring returns the sleeve and the lancet to the first position. The second end 729 of the accommodating portion 725 limits travel of the flange 735 of the struck sleeve 731. The shoulder 722 further facilitates limiting travel of the sleeve 731. The cartridge 721 is fixed in the lancing device 121 such that the cartridge is prevented from moving when the lancet is struck by the firing mechanism. The cartridge bore 723 and sleeve 731 substantially prevent wobble of the lancet 151 during the lancing procedure by providing a straight and smooth path for accurate movement of the lancet.

Alternatively, in each of the embodiments shown in FIGS. 13-17 the lancet and the sleeve can be unitarily formed as a single piece.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:

1. A lancet cartridge assembly for a lancing device, comprising:

a cartridge adapted to be removably received by the lancing device;

a lancet removably received by said cartridge, said lancet being movable between a first position in which a penetrating member connected to said lancet is not exposed outside of the lancing device, and a second position in which said penetrating member is exposed outside of the lancing device to lance a site;

a sleeve surrounding said lancet and positioned between said lancet and said cartridge such that said sleeve moves with said lancet between said first position and second position, said sleeve having a first end and a second end, said second end configured for being struck by a firing mechanism; and a spring for returning said lancet and sleeve to said first position after the site is lanced, where said spring is connected between said cartridge and said lancet to bias said lancet and sleeve to the first position.

2. The lancet cartridge assembly for a lancing device according to claim 1, wherein said cartridge has a bore through which said lancet travels, said bore having an accommodating portion having a diameter larger than that of said lancet; and said lancet having a flange disposed within said accommodating portion of said bore, a length of said accommodating portion controlling a distance traveled by said lancet when struck by a firing mechanism of the lancing device.

3. The lancet cartridge assembly for a lancing device according to claim 1, wherein said spring is connected between said cartridge and said sleeve.

4. The lancet cartridge assembly for a lancing device according to claim 1, wherein said lancet includes a flange and where said first end of said sleeve is adapted to abut said flange of said lancet.

5. The lancet assembly for a lancing cartridge according to claim 1, wherein a first sleeve is disposed rearward of a flange connected to said lancet; and a second sleeve is disposed forward of said lancet flange.

6. The lancet assembly for a lancing cartridge according to claim 5, wherein said spring is connected between said cartridge and said second sleeve.

7. The lancet assembly for a lancing cartridge according to claim 6, wherein said cartridge has a bore through which said lancet and said first and second sleeves travel, said bore having an accommodating portion having a diameter larger than that of said bore; and said second sleeve having a flange disposed within said accommodating portion of said bore, a length of said accommodating portion controlling a distance traveled by said second sleeve when said first sleeve is struck by a firing mechanism of the lancing device.

8. The lancing device of claim 1 wherein said sleeve includes an outwardly extending protrusion, and said cartridge includes a first open entrance slot to receive said protrusion by inserting said lancet and sleeve into a bore formed in said cartridge, and a second slot connected to said first slot by a connecting portion, where said second slot receives said protrusion to guide said protrusion as said lancet and sleeve move between said first position and said second position.

9. A lancet cartridge assembly for a lancing device comprising:

a cartridge adapted to be removably received by the lancing device;

a lancet received by said cartridge, said lancet being movable between a first position in which a penetrating member connected to said lancet is not exposed outside the lancing device and a second position in which said penetrating member is exposed outside the lancing device to lance a site on a patient;

a sleeve surrounding said lancet and positioned between said lancet and said cartridge such that said sleeve moves with said lancet between said first position and said second position;

said cartridge having a bore through which said lancet and said sleeve travel, said bore having an accommodating portion having a diameter larger than that of said bore; and said sleeve having a flange disposed within said accommodating portion of said bore, a length of said accommodating portion controlling a distance traveled by said lancet and sleeve when said sleeve is struck by a firing mechanism of the lancing device; and a spring for returning said lancet and sleeve to said first position after the site is lanced.

10. A lancing device, comprising:

a housing;

a cartridge removably connected to said housing;

a lancet removably received by said cartridge, said lancet being movable between a first position in which a penetrating member connected to said lancet is not exposed outside of said housing, and a second position in which said penetrating member is exposed outside of said housing to lance a site;

a sleeve surrounding said lancet and positioned between said lancet and said cartridge such that said sleeve moves with said lancet between said first and second position; and a spring directly contacting said lancet for returning said lancet and sleeve to said first position after the site is lanced.

11. The lancing device according to claim 10, wherein said spring is connected between said cartridge and said lancet.

12. The lancing device according to claim 10, wherein said cartridge has a bore through which said lancet travels, said bore having an accommodating portion having a larger diameter; and said lancet having a flange disposed within said accommodating portion of said bore, a length of said accommodating portion controlling a distance traveled by said lancet when struck by a firing mechanism of the lancing device.

13. The lancing device according to claim 10, wherein said sleeve is removable from said cartridge and said sleeve.

14. The lancing device according to claim 10, wherein said cartridge has a bore through which said lancet and said sleeve travel, said bore having an accommodating portion having a diameter larger than that of said bore; and said sleeve having a flange disposed within said accommodating portion of said bore, a length of said accommodating portion controlling a distance traveled by said sleeve when said sleeve is struck by a firing mechanism of the lancing device.

15. The lancing device according to claim 10, wherein a protrusion extends outwardly from said sleeve and is received within a slot in said cartridge, said slot guiding said protrusion as said lancet moves between said first and second positions.

16. A method of lancing a site using a lancing device, comprising the steps of:

installing a cartridge having a removable lancet in the lancing device, a sleeve surrounding said lancet and said cartridge such that said sleeve moves with said lancet between said first position and said second position, said sleeve having a first end and a second end, said second end configured for being struck by a firing mechanism, and a spring directly engaging said lancet for returning said lancet and sleeve to said first position after the site is lanced;

using the lancet to lance the site;

removing the cartridge from the lancing device; and removing the used lancet from the cartridge and installing a new lancet.

17. The method of lancing using a lancing device according to claim 16, wherein replacing the used lancet comprises replacing the cartridge with a new cartridge.

18. The method of claim 16, where said lancet includes a flange, said lancet has an outwardly extending flange, and said sleeve includes a first end to abut said flange.

19. The method of claim 16, wherein a protrusion extends outwardly from said sleeve and is received within a slot in said cartridge, said slot guiding said protrusion as said lancet moves between said first and second positions.

* * * * *